United States Patent [19]

Kiefer et al.

[11] Patent Number: 5,462,725

[45] Date of Patent: Oct. 31, 1995

[54] 2-PYRIDYLMETHYLENEPOLY-AZAMACROCYCLOPHOSPHONIC ACIDS, COMPLEXES AND DERIVATIVES THEREOF, FOR USE AS CONTRAST AGENTS

[75] Inventors: Garry E. Kiefer, Lake Jackson; Won D. Kim, Richardson, both of Tex.

[73] Assignee: The Dow Chemical Company, Midland, Mich.

[21] Appl. No.: 57,588

[22] Filed: May 6, 1993

[51] Int. Cl.⁶ .................. A61K 49/00; A61B 5/055; C07D 401/06
[52] U.S. Cl. .................. 424/9.363; 436/173; 534/15; 534/16; 540/465; 540/474; 514/79; 514/183; 514/340; 128/653.4
[58] Field of Search .................. 540/465, 474; 514/79, 183, 340; 424/9; 534/15, 16; 436/173; 128/653.4

[56] References Cited

U.S. PATENT DOCUMENTS

| | | | |
|---|---|---|---|
| 2,609,390 | 9/1952 | Bersworth | 260/500 |
| 3,331,773 | 7/1967 | Gunderson | 210/58 |
| 3,336,221 | 8/1967 | Ralston | 210/58 |
| 3,434,969 | 3/1969 | Ralston | 210/58 |
| 4,880,008 | 11/1989 | Lauffer | 128/654 |
| 4,899,755 | 2/1990 | Lauffer | 128/654 |
| 4,980,148 | 12/1990 | Dean | 424/9 |
| 5,374,416 | 12/1994 | Rousseaux et al. | 424/2 |

FOREIGN PATENT DOCUMENTS

WO92/12978  8/1992  WIPO .................. 540/474

OTHER PUBLICATIONS

Rousseaux et al, Chemical Abstract vol. 118, No. 38963; (1992).
Chelating Agents and Metal Chelants, Dwyer & Mellor, Academic Press (1964), Chapter 7.
I. K. Adzamli et al., J. Med Chem., 32, 139, 144 (1989).
C. J. Broan et al., J. Chem. Soc., Chem. Commun., 1739–1741 (1990).
C. J. Broan et al., J. Chem. Soc., Chem Commun., 1738–1739 (1990).

Primary Examiner—Philip I. Datlow
Attorney, Agent, or Firm—Karen L. Kimble

[57] ABSTRACT

2-Pyridylmethylenepolyazamacrocyclophosphonic acid compounds and their derivatives are disclosed which may form inert complexes with Gd, Mn or Fe ions. The overall charge of the complex can be varied to alter the in vivo biolocalization. The complexes are useful as contrast agents for diagnostic purposes.

13 Claims, No Drawings

2-PYRIDYLMETHYLENEPOLY-AZAMACROCYCLOPHOSPHONIC ACIDS, COMPLEXES AND DERIVATIVES THEREOF, FOR USE AS CONTRAST AGENTS

This invention concerns ligands that are 2-pyridylmethylenepolyazamacrocyclophosphonic acids, complexes and derivatives thereof, for use as contrast agents in magnetic resonance imaging (MRI). To better understand this invention, a brief background on MRI is provided in the following section.

BACKGROUND OF THE INVENTION

MRI is a non-invasive diagnostic technique which produces well resolved cross-sectional images of soft tissue within an animal body, preferably a human body. This technique is based upon the property of certain atomic nuclei (e.g. water protons) which possess a magnetic moment [as defined by mathematical equations; see G. M. Barrow, *Physical Chemistry*, 3rd Ed., McGraw-Hill, NY (1973)] to align in an applied magnetic field. Once aligned, this equilibrium state can be perturbed by applying an external radio frequency (RF) pulse which causes the protons to be tilted out of alignment with the magnetic field. When the RF pulse is terminated, the nuclei return to their equilibrium state and the time required for this to occur is known as the relaxation time. The relaxation time consists of two parameters known as spin-lattice (T1) and spin-spin (T2) relaxation and it is these relaxation measurements which give information on the degree of molecular organization and interaction of protons with the surrounding environment.

Since the water content of living tissue is substantial and variations in content and environment exist among tissue types, diagnostic images of biological organisms are obtained which reflect proton density and relaxation times. The greater the differences in relaxation times (T1 and T2) of protons present in tissue being examined, the greater will be the contrast in the obtained image [*J. Magnetic Resonance* 33, 83–106 (1979)].

It is known that paramagnetic chelates possessing a symmetric electronic ground state can dramatically affect the T1 and T2 relaxation rates of juxtaposed water protons and that the effectiveness of the chelate in this regard is related, in part, to the number of unpaired electrons producing the magnetic moment [*Magnetic Resonance Annual*, 231–266, Raven Press, NY (1985)]. It has also been shown that when a paramagnetic chelate of this type is administered to a living animal, its effect on the T1 and T2 of various tissues can be directly observed in the magnetic resonance (MR) images with increased contrast being observed in the areas of chelate localization. It has therefore been proposed that stable, non-toxic paramagnetic chelates be administered to animals in order to increase the diagnostic information obtained by MRI [*Frontiers of Biol. Energetics I*, 752–759 (1978); *J. Nucl. Med.* 25, 506–513 (1984); *Proc. of NMR Imaging Symp.* (Oct. 26–27, 1980); F. A. Cotton et al., *Adv. Inorg. Chem.* 634–639 (1966)]. Paramagnetic metal chelates used in this manner are referred to as contrast enhancement agents or contrast agents.

There are a number of paramagnetic metal ions which can be considered when undertaking the design of an MRI contrast agent. In practice, however, the most useful paramagnetic metal ions are gadolinium ($Gd^{+3}$), iron ($Fe^{+3}$), manganese ($Mn^{+2}$) and ($Mn^{+3}$), and chromium ($Cr^{+3}$), because these ions exert the greatest effect on water protons by virtue of their large magnetic moments. In a non-complexed form (e.g. $GdCl_3$), these metal ions are toxic to an animal, thereby precluding their use in the simple salt form. Therefore, a fundamental role of the organic chelating agent (also referred to as a ligand) is to render the paramagnetic metal non-toxic to the animal while preserving its desirable influence on T1 and T2 relaxation rates of the surrounding water protons.

Art in the MRI field is quite extensive, such that the following summary, not intended to be exhaustive, is provided only as a review of this area and other compounds that are possibly similar in structure. U.S. Pat. No. 4,899,755 discloses a method of alternating the proton NMR relaxation times in the liver or bile duct of an animal using $Fe^{+3}$-ethylene-bis(2-hydroxyphenylglycine) complexes and its derivatives, and suggests among various other compounds the possible use of a pyridine macrocyclomethylenecarboxylic acid. U.S. Pat. No. 4,880,008 (a CIP of U.S. Pat. No. 4,899,755) discloses additional imaging data for liver tissue of rats, but without any additional complexes being shown. U.S. Pat. No. 4,980,148 disclose gadolinium complexes for MRI which are non-cyclic compounds. C. J. Broan et al., *J. Chem. Soc., Chem. Commun.*, 1739–1741 (1990) describe some bifunctional macrocyclic phosphinic acid compounds. C. J. Broan et al., *J. Chem. Soc., Chem. Commun.*, 1738–1739 (1990) describe compounds that are triazabicyclo compounds. I. K. Adzamli et al., *J. Med. Chem.* 32, 139–144 (1989) describes acyclic phosphonate derivatives of gadolinium complexes for NMR imaging.

At the present time, the only commercial contrast agents available in the U.S. are the complex of gadolinium with diethylenetriaminepentaacetic acid (DTPA-$Gd^{+3}$—Magnevist™ by Shering) and a DO3A derivative [1,4,7-tris(carboxymethyl)-10-(2-hydroxypropyl)-1,4,7,10-tetraazacyclododecanato]gadolinium (Prohance™ by Squibb). Magnevist™ and Prohance™ are considered as non-specific/perfusion agents since they freely distribute in extracellular fluid followed by efficient elimination through the renal system. Magnevist™ has proven to be extremely valuable in the diagnosis of brain lesions since the accompanying breakdown of the blood/brain barrier allows perfusion of the contrast agent into the affected regions. In addition to Magnevist™, Guerbet is commercially marketing a macrocyclic perfusion agent [1,4,7,10-tetrakis(carboxymethyl)-1,4,7,10-tetraazacyclododecanato] gadolinium (Dotarem™) which presently is only available in Europe. Prohance™ is shown to have fewer side effects than Magnevist™. A number of other potential contrast agents are in various stages of development.

SUMMARY OF THE INVENTION

The present invention is directed to novel ligands that are 2-pyridylmethylenepolyazamacrocyclic compounds, and derivatives thereof, of the formula

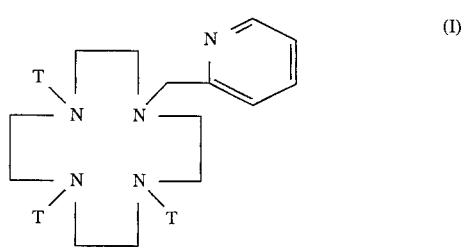

wherein:

T is independently —CH$_2$—COOH, $$-CH_2-\underset{R}{\underset{|}{\overset{O}{\overset{\|}{P}}}}-OH \quad \text{or} \quad -\underset{CO_2H}{\underset{|}{CH}}-\underset{R^2}{\overset{R^1}{\bigcirc}};$$

where:

R is OH, C$_1$–C$_5$ alkyl or —O—(C$_1$–C$_5$ alkyl);

R$^1$ is OH or OCH$_3$;

R$^2$ is NO$_2$, NH$_2$, isothiocyanato, semicarbazido, thiosemicarbazido, maleimido, bromoacetamido or carboxyl;

with the proviso that only one T moiety is $$-\underset{CO_2H}{\underset{|}{CH}}-\underset{R^2}{\overset{R^1}{\bigcirc}};$$

where R$^1$ and R$^2$ are defined as before; or pharmaceutically-acceptable salts thereof.

When the above ligands of Formula (I) have:

all T equal CH$_2$—P(O)ROH, where R is OH, or the pharmaceutically-acceptable salts thereof, the ligands are referred to herein as PD3P;

all T equal CH$_2$—COOH, or the pharmaceutically-acceptable salts thereof, the ligands are referred to herein as PD3A;

all T equal CH$_2$—P(O)ROH, where R is —O—(C$_1$–C$_5$ alkyl), or the pharmaceutically-acceptable salts thereof, the ligands are referred to herein as PD3(O—Alk)P; and all T equal CH$_2$—P(O)ROH, where R is C$_1$–C$_5$ alkyl, or the pharmaceutically-acceptable salts thereof, the ligands are referred to herein as PD3(Alk)P.

The complexes of this invention can be designed to provide a specific overall charge which advantageously influences the in vivo biolocalization and image contrast. For example, when the metal ion is +3 the following can be obtained:

an overall charge of −3—when Formula (I) is PD3P, which are useful as calcific tissue contrast agents;

an overall charge of −2—when Formula (I) has two T equal to —CH$_2$—PO$_3$H$_2$ and one T has a COOH group present, which are useful as calcific tissue contrast agents;

an overall charge of −1—when Formula (I) has one T equal to —CH$_2$—PO$_3$H$_2$ and the other T has a COOH group present, which are useful as calcific tissue contrast agents;

an overall neutral charge of 0—when Formula (I) has one T equal to —CH$_2$—PO$_3$HR where R is —O—(C$_1$–C$_5$ alkyl) or C$_1$–C$_5$ alkyl and two T have a COOH group present; or all three T equal —CH$_2$—PO$_3$HR where R is —O—(C$_1$–C$_5$ alkyl) or C$_1$–C$_5$ alkyl; or all three T equal —CH$_2$—COOH (PD3A), which are useful as general perfusion, blood pool, brain or liver contrast agents.

The complexes may be formulated to be in a pharmaceutically acceptable form for administration to an animal.

When one T term is $$-\underset{CO_2H}{\underset{|}{CH}}-\underset{R^2}{\overset{R^1}{\bigcirc}};$$

where R$^1$ and R$^2$ are defined as before, then the compound is a bifunctional ligand/complex and may be linked through R$^2$ to a biologically active molecule.

DETAILED DESCRIPTION OF THE INVENTION

The compounds of Formula (I) are numbered for nomenclature purposes as follows:

(I)

One aspect of the present invention concerns development of contrast agents having synthetic modifications to the paramagnetic chelate enabling site specific delivery of the contrast agent to a desired tissue. The advantage being increased contrast in the areas of interest based upon tissue affinity as opposed to contrast arising from non-specific perfusion which may or may not be apparent with an extracellular agent. The specificity of the ligand of Formula (I) may be controlled by adjusting the total charge and lipophilic character of the complex. The overall range of the charge of the complex is from −3 to 0 as indicated above. For example, for a complex having 3 PO$_3$H$_2$ groups (PD3P), the overall charge is highly negative and bone uptake is expected; whereas when the overall charge of the complex is 0 (thus neutral, PD3A, PD3(O—Alk)P, and PD3(Alk)P), the complex may have the ability to cross the blood brain barrier and normal brain uptake may be possible. Unexpectly, for a complex having an overall charge of 0 [PD3(O—Pr)P], the complex displays liver uptake.

While not wishing to be bound by theory, it is believed that when a charged complex of the invention is made (e.g. possibly −3 for bone, −1 for liver, or +1 for heart), the variations in that chelate ionic charge can influence biolocalization.

Tissue specificity may also be realized by ionic or covalent attachment of the chelate to a naturally occurring or synthetic molecule (e.g. through R$^2$) having specificity for a desired target tissue. One possible application of this approach is through the use of chelate conjugated monoclonal antibodies which would transport the paramagnetic chelate to diseased tissue enabling visualization by MRI. In addition, attachment of a paramagnetic chelate to a macromolecule can further increase the contrast agent efficiency resulting in improved contrast relative to the unbound chelate. Recent work by Lauffer (U.S. Pat. Nos. 4,880,008 and 4,899,755) has demonstrated that variations in lipophilicity can result in tissue-specific agents and that increased lipophilic character favors non-covalent interactions with blood proteins resulting in enhancement of relaxivity.

Typical DO3A derivatives in which non-coordinating N-substituents are present generate neutral lanthanide chelates but have been found to be kinetically labile under acidic conditions. The DO3A derivative PROHANCE™ gains added kinetic stability by virtue of a pendant hydroxyl moiety which can coordinate to the metal ion but may alter the overall chelate ionic character. In contrasty the present invention relates to a group of DO3A derivatives of Formula (I) which possess a 2-pyridyl pendant moiety which forms a coordinate bond without altering the overall chelate ionic character. In addition it has now beeen found that the 2-pyridyl substituent adds kenetic stability to the chelate under acidic conditions (pH below about 7). Chelates of this invention in which the ligation moities are PO3HR where R is $-O-(C_1-C_5$ alkyl) have demonstrated potential as liver imaging agents.

The terms used in Formula (I) and for this invention are further defined as follows. "$C_1-C_5$ alkyl", include both straight and branched chain alkyl groups. An "animal" includes a warmblooded mammal, preferably a human being. As used herein, "complex" refers to a complex of the compound of the invention, e.g. Formula (I), complexed with a metal ion, where at least one metal atom is chelated or sequestered.

"Biologically active material" refers to a dextran, peptide, or molecules that have specific affinity for a receptor, or preferably antibodies or antibody fragments.

"Antibody" refers to any polyclonal, monoclonal, chimeric antibody or heteroantibody, preferably a monoclonal antibody; "antibody fragment" includes Fab fragments and $F(ab')_2$ fragments, and any portion of an antibody having specificity toward a desired epitope or epitopes. When using the term "radioactive metal chelate/antibody conjugate" or "conjugate", the "antibody" is meant to include whole antibodies and/or antibody fragments, including semisynthetic or genetically engineered variants thereof. Possible antibodies are 1116-NS-19-9 (anti-colorectal carcinoma), 1116-NS-3d (anti-CEA), 703D4 (anti-human lung cancer), 704A1 (anti-human lung cancer) and B72.3. The hybridoma cell lines 1116-NS-19-9, 1116-NS-3d, 703D4, 704A1, CC49, CC83 and B72.3 are deposited with the American Type Culture Collection, having the accession numbers ATCC HB 8059, ATCC CRL 8019, ATCC HB 8301, ATCC HB 8302, ATCC HB 9459, ATCC HB 9453 and ATCC HB 8108, respectively.

The bifunctional chelating agents described herein (represented by Formula I) can be used to chelate or sequester the metal ions so as to form metal ion chelates (also referred to herein as "complexes"). The complexes, because of the presence of the functionalizing moiety (represented by $R^2$ in Formula I), can be covalently attached to biologically active materials, such as dextran, molecules that have specific affinity for a receptor, or preferably covalently attached to antibodies or antibody fragments. Thus the complexes described herein may be covalently attached to an antibody or antibody fragment or have specific affinity for a receptor and are referred to herein as "conjugates".

As used herein, "pharmaceutically-acceptable salts" means any salt or mixtures of salts of a compound of Formula (I) which is sufficiently non-toxic to be useful in diagnosis of animals, preferably mammals. Thus, the salts are useful in accordance with this invention. Representative of those salts formed by standard reactions from both organic and inorganic sources includes for examples sulfuric, hydrochloric, phosphoric, acetic, succinic, citric, lactic, maleic, fumaric, palmitic, cholic, palmoic, mucic, glutamic, gluconic acid, d-camphoric, glutaric, glycolic, phthalic, tartaric, formic, lauric, steric, salicylic, methanesulfonic, benzenesulfonic, sorbic, picric, benzoic, cinnamic acids and other suitable acids. Also included are salts formed by standard reactions from both organic and inorganic sources such as ammonium or 1-deoxy-1-(methylamino)-D-glucitol, alkali metal ions, alkaline earth metal ions, and other similar ions. Particularly preferred are the salts of the compounds of Formula (I) where the salt is potassium, sodium, or ammonium. Also included are mixtures of the above salts.

DETAILED DESCRIPTION OF THE PROCESS

The compounds of Formula (I) are prepared by various processes. Typical general synthetic approaches to such processes are provided by the reaction schemes given below.

The starting material of Formula (II) shown in these Schemes is prepared by alkylation of cyclen (1,4,7,10-tetraazacyclododecane) with 2-chloromethyl pyridine at room temperature in an inert organic solvent such as choloform.

In Scheme 1, the compounds of Formula (I) are prepared wherein all T moieties are $-CH_2-COOH$.

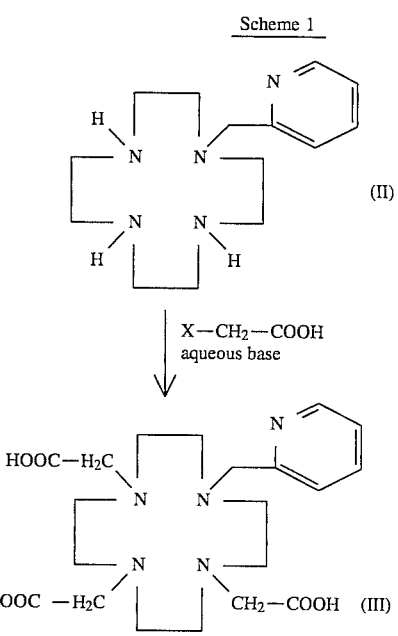

The aqueous base is alkali metal hydroxide, such as sodium hydroxide or potassium hydroxide. The pH of the reaction is maintained about 8–12. Temperature is between about 60°–90° C., and pressure is not critical so that ambient pressure is used.

In Scheme 2, the compounds of Formula (I) are prepared wherein all T moieties are

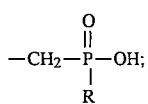

where:

R is OH.

Scheme 2

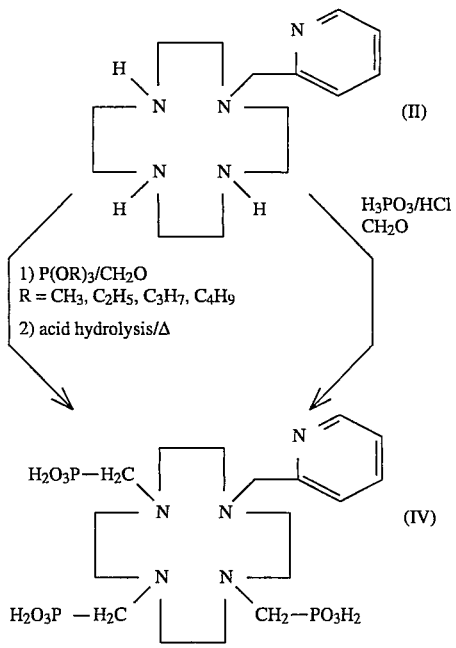

The hydrolysis in Scheme 2 is done by known aqueous acid conditions, such as using 3 to 12M hydrochloric acid. The pH of the reaction is maintained below 3. Temperature is at reflux. Pressure is not critical so that ambient pressure is used. Alternatively, when the reaction is run in one step, phosphorous acid, hydrochloric acid and excess formaldehyde are used. The pH of the reaction is below 2. Temperature is at reflux. Pressure is not critical so that ambient pressure is used.

In Scheme 3, the compounds of Formula (I) are prepared wherein all T moieties are

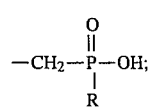

where:

R is —O—($C_1$–$C_5$ alkyl).

Scheme 3

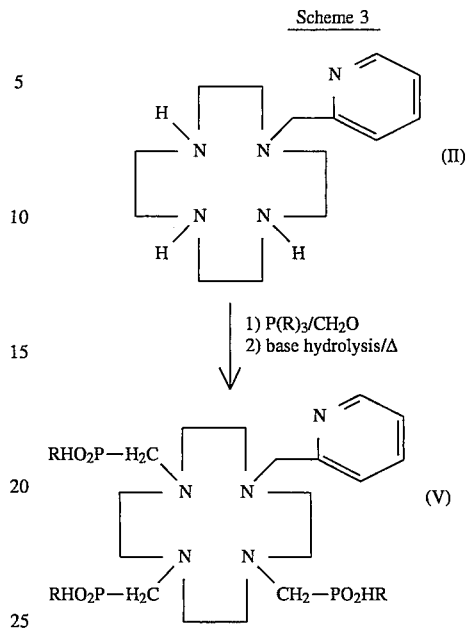

wherein:

R is —O—($C_1$–$C_5$ alkyl).

The hydrolysis in Scheme 3 is done under known aqueous basic conditions, such as using excess alkali metal hydroxide, such as sodium or potassium hydroxide. The pH of the reaction is above 9. Temperature is at reflux. Pressure is not critical so that ambient pressure is used.

In Scheme 4, the compounds of Formula (I) are prepared wherein all T moieties are

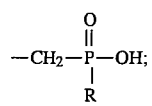

where:

R is $C_1$–$C_5$ alkyl.

Scheme 4 shows the preparation of the compounds of Formula (I) when R is methyl.

Scheme 4

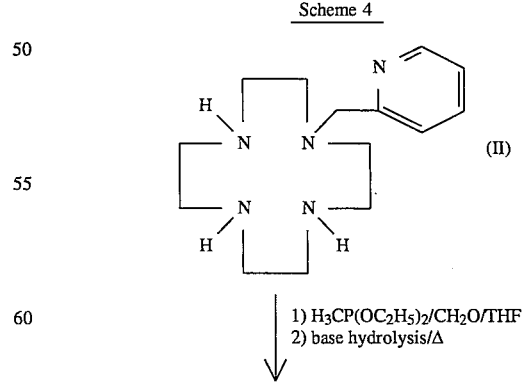

-continued
Scheme 4

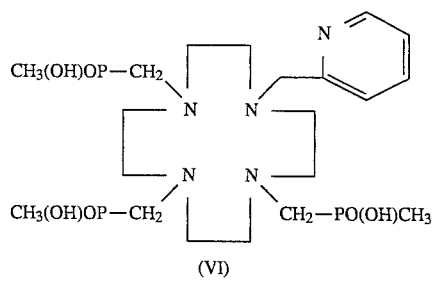

(VI)

The hydrolysis in Scheme 4 is done under known aqueous basic conditions, such as using excess alkali metal hydroxide, such as sodium or potassium hydroxide. The pH of the reaction is above 9. Temperature is at reflux. Pressure is not critical so that ambient pressure is used.

Scheme 5 shows the preparation of the compounds of Formula (I) when R is ethyl.

Scheme 5

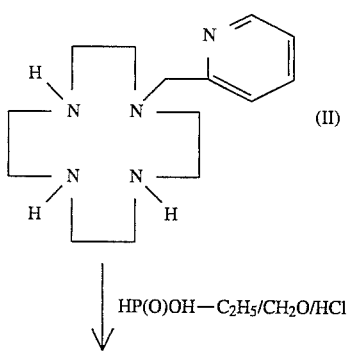
(II)

↓ HP(O)OH—$C_2H_5$/$CH_2O$/HCl

-continued
Scheme 5

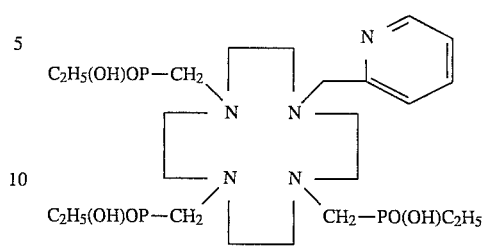

The reaction in Scheme 5 is under acidic conditions with a hydrochloric acid. The pH of the reaction is below 3. Temperature is at reflux. Pressure is not critical so that ambient pressure is used.

Scheme 6 shows the preparation of the compounds of Formula (I) when T has a bifunctional moiety.

Scheme 6

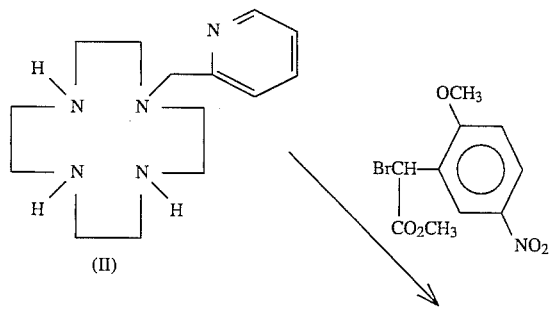

Scheme 6
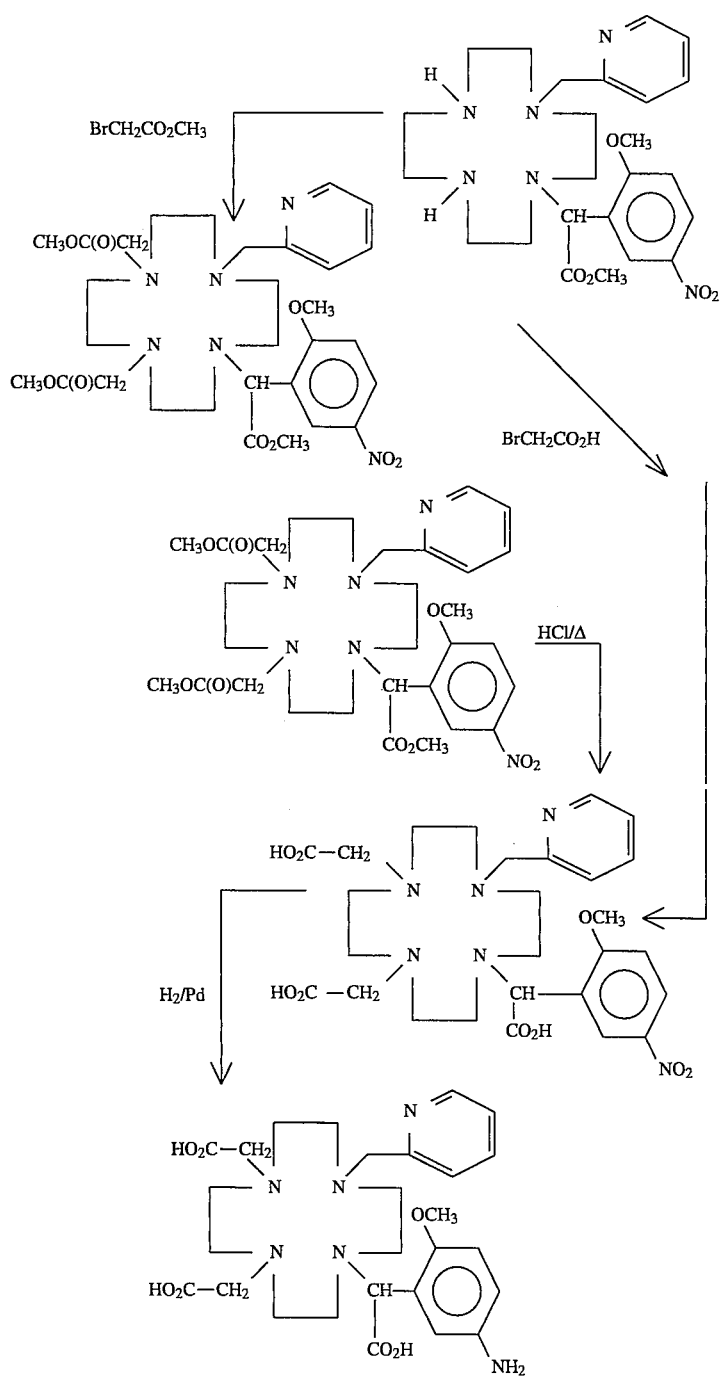
Scheme 7 shows the preparation of the compounds of Formula (I) when one T is PO$_3$HR where R is defined as in Formula (I) and the other two T are COOH.

Scheme 7

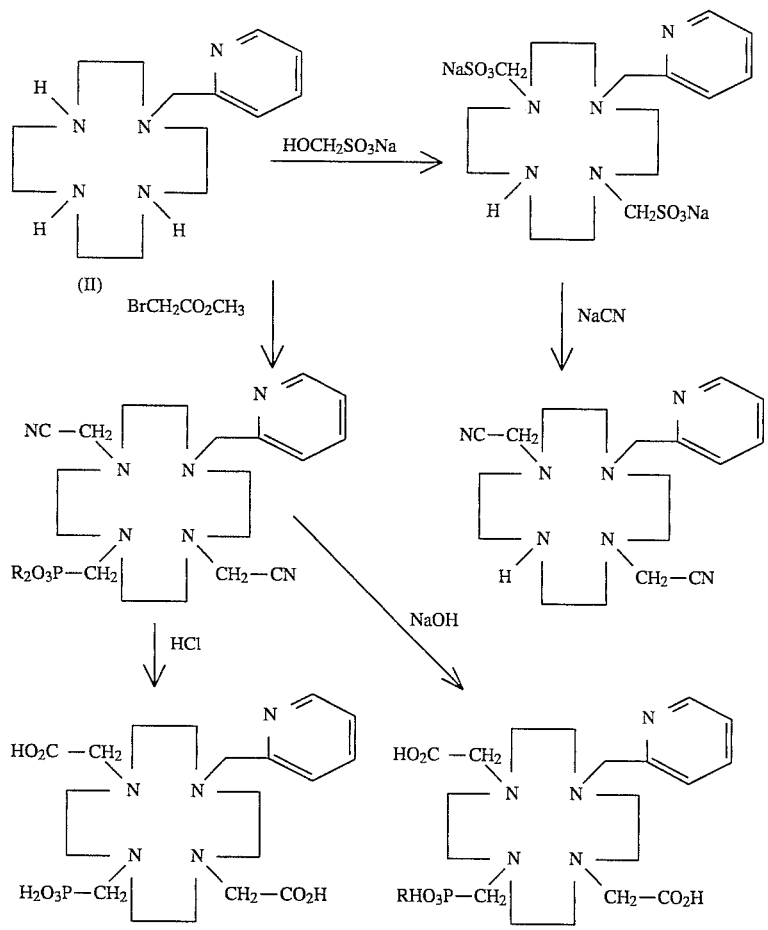

In Scheme 7 the hydrolysis steps are done as described in prior schemes. The formaldehyde/bisulfite addition complex reaction is done aqueous basic conditions to give selective alkylation at the 4,10-positions. The phosphonate group is then indroducted selectively at the 7-position.

In the above Schemes, the general process discription illustrates specific steps that may be used to accomplish a desired reaction step. The general description of these process steps follows.

The carboxylate derivative described in Scheme 1 are prepared by conventional alkylation procedures utilizing chloro- or bromo-acetic acid under basic aqueous conditions.

The phosphonic acid derivatives outlined in Scheme 2 can be prepared by initial alkylation of the amine with a trialkyl phosphite and paraformaldehyde, resulting in an organic soluble perester. This ester is then hydrolyzed under refluxing acid conditions to give the desired aminophosphonic acids. Alternatively, the phosphonic acid can be prepared under acidic conditions by employing phosphorous acid in combination with formaldehyde and hydrochloric acid.

Phosphonate half esters are prepared as shown in Scheme 3 by initial formation of the dialkyl phosphonate ester, followed by hydrolysis under basic conditions. Base hydrolysis gives exclusive conversion to the half ester.

Scheme 4 illustrates the metholodgy for synthesizing the methyl phosphinate derivatives using diethoxymethylphosphine as the nucleophile and paraformaldehyde. Condensation can be conducted in solvents such as tetrahydrofuran (THF), dimethylformamide (DMF), dioxane, acetonitrile, or alcoholic media. The resulting phosphinate ester is then hydrolyzed under acidic conditions (e.g. 6N HCl, 80°–100° C.) or basic conditions (excess base, 40°–100° C.) to give the corresponding methylphosphonic acid. Alternatively, as outlined in Scheme 5, the method devised by A. D. Sherry et al. (*Inorg. Chem.*, submitted 1991) using ethylphosphonic acid generated in situ can be used to obtain phosphinate derivatives having increased lipophilic character.

Scheme 6 illustrates the preparation of bifunctional compounds of Formula (I) which may then be attached to a biologically active material.

Scheme 7 shows a general procedure for the selective alkylation of the 4,10-positions using the formaldehyde/bisulfite addition compound. The resulting intermediate is converted to the corresponding nitrile, followed by introduction of the phosphonate moiety at the the 7-position. Acid or base hydrolysis yields the corresponding hydrolyzed final products.

The metal ions used to form the complexes of this invention are $Gd^{+3}$, $Mn^{+2}$, $Fe^{+3}$ and available commercially, e.g. from Aldrich Chemical Company. The anion present is halide, preferrably chloride, or salt free (metal oxide).

A "paramagnetic nuclide" of this invention means a metal ion which displays spin angular momentum and/or orbital angular momentum. The two types of momentum combine to give the observed paramagnetic moment in a manner that depends largely on the atoms bearing the unpaired electron and, to a lesser extent, upon the environment of such atoms. The paramagnetic nuclides found to be useful in the practice of the invention are gadolinium ($Gd^{+3}$), iron ($Fe^{+3}$) and manganese ($Mn^{+2}$), with $Gd^{+3}$ being preferred.

The complexes are prepared by methods well known in the art. Thus, for example, see Chelating Agents and Metal Chelates, Dwyer & Mellor, Academic Press (1964), Chapter 7. See also methods for making amino acids in *Synthetic Production and Utilization of Amino Acids,* (edited by Kameko, et al.) John Wiley & Sons (1974). An example of the preparation of a complex involves reacting a bicyclopolyazamacrocyclophosphonic acid with the metal ion under aqueous conditions at a pH from 5 to 7. The complex formed is by a chemical bond and results in a stable paramagnetic nuclide composition, e.g. stable to the disassociation of the paramagnetic nuclide from the ligand.

The complexes of the present invention are administered at a ligand to metal molar ratio of at least about 1:1, preferably from 1:1 to 3:1, more preferably from 1:1 to 1.5:1. A large excess of ligand is undesirable since uncomplexed ligand may be toxic to the animal or may result in cardiac arrest or hypocalcemic convulsions.

This invention is used with a physiologically acceptable carrier, excipient or vehicle therefore. The methods for preparing such formulations are well known. The formulations may be in the form of a suspension, injectable solution or other suitable formulations. Physiologically acceptable suspending media, with or without adjuvants, may be used.

An "effective amount" of the formulation is used for diagnosis. The dose will vary depending on the disease and physical parameters of the animal, such as weight. In vivo diagnostics are also contemplated using formulations of this invention.

Other uses of some of the chelants of the present invention may include the removal of undesirable metals (i.e. iron) from the body, attachment to polymeric supports for various purposes, e.g. as diagnostic agents, and removal of metal ions by selective extraction. The ligands of Formula (I) having in at least two R terms T equal to —$CH_2$—P(O)$R^1$OH may be used for metal ion control as scale inhibitors. Some of these ligands can be used in less than stoichiometric amounts. Similar uses are known for compounds described in U.S. Pat. Nos. 2,609,390; 3,331,773; 3,336,221; and 3,434,969.

The invention will be further clarified by a consideration of the following examples, which are intended to be purely exemplary of the present invention.

Some terms used in the following examples are defined as follows:

LC=liquid chromatography, purifications were carried out at low pressure using Dionex 2010i system fitted with a hand-packed Q-Sepharose™ anion exchange column (23×2 cm).
DMF=dimethylforamide.
AcOH=acetic acid.
g=gram(s).
mg=milligrams.
kg=kilogram(s).
mL=milliliter(s).
µL=microliter(s).

pH Stability General Procedure

A stock $^{159}GdCl_3$ (or $^{153}SmCl_3$) solution was prepared by adding 2 µL of 3×10$^{-4}$M $^{159}GDCl_3$ in 0.1N HCl to 2 mL of a 3×10$^{-4}$M $GdCl_3$ carrier solution. Appropriate ligand solutions were then prepared in deionized water. The 1:1 ligand/ metal complexes were then prepared by combining the ligands (dissolved in 100–500 µL of deionized water) with 2 mL of the stock $^{159}GDCl_3$ solution, followed by through mixing to give an acidic solution (pH=2). The pH of the solution was then raised to 7.0 using 0.1N NaOH. The percent metal as a complex was then determined by passing a sample of the complex solution through a Sephadex™ G-50 column, eluting with 4:1 saline (85% NaCl/$NH_4OH$) and collecting 2×3 mL fractions. The amount of radioactivity in the combined elutions was then compared with that left on the resin (non-complexed metal is retained on the resin). The pH stability profile was generated by adjusting the pH of an aliquot of the complex solution using 1M NaOH or 1M HCl and determining the percent of the metal existing as a complex using the ion exchange method described above. The Sm results are known by experminal comparison to be identical for complexation and biodistribution of the ligands of this invention.

SYNTHESIS OF LIGANDS

General Materials and Methods

All reagents were obtained from commercial suppliers and used as received without further purification. NMR spectra were recorded on a Bruker AC- 250 MHz spectrometer equipped with a multi-nuclear quad probe ($^1H$, $^{13}C$, $^{31}P$, and $^{19}F$) at 297° K. unless otherwise indicated. $^1H$ spectra in $D_2O$ were recorded by employing solvent suppression pulse sequence ("PRESAT" homonuclear presaturation). $^1H$ spectra are referenced to residual chloroform (in $CDCl_3$) at δ7.26 or external dioxane (in $D_2O$) at δ3.55. $^{13}C$ and $^{31}P$ spectra reported are proton decoupled (broad band). Assignments of $^{13}C$ {$^1H$} chemical shifts were aided by DEPT (Distortionless Enhancement by Polarization Transfer) experiments. $^{13}C$ {$^1H$} spectra are referenced to center peak of $CDCl_3$ at δ77.00 (in $CDCl_3$) and external dioxane at δ66.66 (in $D_2O$). $^{31}P$ {$^1H$} spectra were referenced to external 85% $H_3PO_4$ at δ0.00. Melting points were determined by capilliary melt methods and were uncorrected. Semipreparative ion-exchange chromatographic separations were performed at low pressure (<600 psi) using a standard glass column fitted with hand-packed Q-Sepharose™ (anion exchange) or SP-Sepharose™ (cation exchange) glass column, and with on-line UV detector at 263 nm for eluent monitoring. GC/MS spectra were performed on a Hewlett Packard 5890A Gas Chromatograph/5970 Mass Selective Detector.

STARTING MATERIALS

Example A

Preparation of N-(2-pyridylmethyl)-1,4,7,10-tetraazacyclododecane

A 2-picolyl chloride solution in chloroform was prepared by basifying 3 mL of an aqueous solution of 1.03 g (6.3 mmol) of 2-picolyl chloride hydrochloride to pH>14 and extracting into chloroform. To a stirred chloroform solution of 2.03 g (11.8 mmol) of 1,4,7,10-tetraazacyclododecane was added 10 mL of the prepared 2-picolyl chloride solution in chloroform in one portion. After stirring at temperature for 30 min, the reaction mixture was concentrated in vacuo to give a residue which was chromatographed on sffica gel (column, 2.5×20 cm), eluting with $CHCl_3$:$CH_3OH$: $NH_4OH$ (10:4:1), $R_f$=0.29 on $SiO_2$ plate. After concentration of eluent, the monoalkylated product was isolated a as thick pale yellow liquid, which upon standing solidified to give 1.17 g of an off-white powder (72%, based on 2-picolyl chloride), and further characterized by:

$^1$H NMR (CDCl$_3$) δ 2.54–2.82 (m, 16H), 3.75 (s, 2H), 7.11–7.14 (m, 1H), 7.42–7.46 (m, 1H), 7.64–7.65 (m, 1H), 8.46–8.48 (m, 1H); and $^{13}$C {$^1$H} NMR (CDCl$_3$) δ 45.02, 46.31, 47.04, 51.51, 61.03, 122.04, 122.87, 136.61, 148.83, 150.53.

Example B

Preparation of N-(2-pyridylmethyl)-N',N'',N'''-tris(methylenediethylphosphonate)-1,4,7,10-tetraazacyclododecane To 331 mg (1.27 mmol) of N-(2-pyridylmethyl)- 1,4,7,10-tetraazacyclododecane, prepared in Example A, was combined 229 mg (7.63 mmol, excess) of paraformaldehyde and 1.3 mL of 1.27 g (7.62 mmol, excess) of triethylphosphite. After the mixture was gently stirred for 10 min to obtain a well mixed slurry, it was heated to 90° C. for 1 hr. The excess reagents and the byproducts were removed in vacuo (125° C./0.01 mmHg) to give 896 mg (99%) of the desired product as a yellow oil, and further characterized by:

$^1$H NMR (CDCl$_3$) δ 1.25–1.39 (m, 18H), 2.66–2.95 (m, 22H), 3.71 (s, 2H), 4.01–4.22 (m, 12H), 7.10–7.15 (m, 1H), 7.57– 7.65 (m, 2H), 8.46–8.52 (m, 1H);

$^{13}$C {$^1$H} NMR (CDCl$_3$) δ 16.38, 16.46, 50.45, 50.67, 52.41, 53.19, 53.29, 53.48, 53.58, 61.37, 61.47, 61.52, 121.67, 123.28, 136.19, 148.61, 159.90; and $^{31}$P {$^1$H} NMR (CDCl$_3$, 297K) δ 26.21;

$^{31}$P {$^1$H} NMR (CDCl$_3$, 217K) δ 24.18 (1P), 24.32 (2P).

Example C

Preparation of N-(2-pyridylmethyl)-N',N'',N'''-tris(methylenedipropylphosphonate)-1,4,7,10-tetraazacyclododecane To 445 mg (1.71 mmol) of N-(2-pyridylmethyl)- 1,4,7,10-tetraazacyclododecane, prepared in Example A, was combined 154 mg (5.12 mmol, excess) of paraformaldehyde and 3.5 mL of 3.20 g (5.12 mmol, excess) of tripropylphosphite. After the mixture was gently stirred for 10 min to obtain a well mixed slurry, it was heated to 100° C. for 30 min. The excess reagents and the byproducts were removed in vacuo (4 hr. at 160° C./0.01 mmHg) to give 1.36 g (quantative) of the desired product as a thick yellow oil, and further characterized by:

$^1$H NMR (CDCl$_3$) δ 0.91–1.00 (m, 18H), 1.60–1.76 (m, 12H), 2.67– 2.99 (m, 22H), 3.73 (s, 2H), 3.94–4.08 (m, 12H), 7.12–7.15 (m, 1H), 7.46–7.67 (m, 2H), 8.48–8.52 (m, 1H);

$^{13}$C {$^1$H} NMR (CDCl$_3$) δ 9.93, 10.21, 23.71, 23.80, 50.17, 50.44, 52.38, 53.09, 53.44, 61.44, 66.79, 66.83, 121.61, 123.23, 136.14, 148.54, 159.92; and $^{31}$P {$^1$H} NMR (CDCl$_3$) δ 26.20 (1P), 26.23 (2P).

FINAL PRODUCTS

Ligands: Preparation of dimethylenecarboxylic acids as shown in Scheme 1.

EXAMPLE 1

Preparation of N-(2-pyridylmethyl)-N',N'',N'''-triacetic acid-1,4,7,10-tetraazacyclododecane (PD3A)

To 2 mL of an aqueous solution of 201.4 mg (0.51 mmol) of N-(2-pyridylmethyl)-1,4,7,10-tetraazacyclododecane, prepared by the procedure of Example A, was added 350 mg (2.52 mmol, 65% excess) of bromoacetic acid and the pH of the reaction mixture was maintained above 11 by adding small portions of concentrated sodium hydroxide until no more caustic was needed to keep pH> 11 (~30 min). The reaction mixture was then heated (60° C.) for 1 hr. After the reaction mixture was cooled to room temperature, the pH of the reaction mixture was adjusted to 7 and the neutral solution chromatographed on a cation exchange (SP-Sepharose™) column (1.5×50 cm) eluting first with deionized water then with 1M hydrochloric acid. The acidic fraction which contained product was evaporated to dryness, followed by co-evaporation (azeotrope) with fresh deionized water (3×2 mL) to eliminate excess hydrochloric acid. The final product was isolated as white solid upon freeze-drying of the aqueous solution, and further characterized by:

$^1$H NMR (D$_2$O) δ 2.79–4.13 (m, 24H), 7.88–8.01 (m, 2H), 8.35–8.42 (m, 1H), 8.63–8.66 (m, 1H); and $^{13}$C {$^1$H} NMR (D$_2$O) δ 51.04, 51.25, 53.73, 55.47, 56.00, 56.90, 57.52, 129.86, 131.21, 145.49, 150.82, 153.54, 171.61, 178.76. Ligands: Preparation of dimethylenephosphonate half esters as shown in Scheme 3.

EXAMPLE 2

Preparation of N-(2-pyridylmethyl)-N',N'',N'''-tris(methylenephosphonic acid ethyl ester)-1,4,7,10-tetraazacyclododecane (PD3EP)

N-(2-pyridylmethyl)-N',N'',N'''-tris(methylenediethylphosphonate)- 1,4,7,10-tetraazacyclododecane, 102.7 mg (0.14 mmol), prepared in Example B, was combined with 1 mL of 0.1M of potassium hydroxide and heated at 90° C. for 6 hr. After cooling to room temperature, the aqueous solution was freeze-dried to give a tan solid, which was chromatographed on an anion exchange (Q-Sepharose™) column (1.5×50 cm) eluting first with deionized water, then with 1M hydrochloric acid. Following freeze-drying of the eluent, the product was isolated as a brown solid and further characterized by:

$^1$H NMR (D$_2$O, 338 K) δ 1.41–1.57 (m, 9H), 3.28–3.89 (m, 22H), 4.09–4.64 (m, 8H), 8.22–8.26 (m, 2H), 8.70–8.75 (m, 1H), 9.00– 9.12 (m, 1H); and $^{13}$C {$^1$H} NMR (D$_2$O, 338 K) δ 19.41, 19.51, 52.58, 53.00, 52.31, 53.75, 53.82, 56.04, 59.53, 64.60, 64.76, 129.86, 131.41, 147.31, 149.06, 154.34; and $^{31}$P {$^1$H} NMR (D$_2$O, 338K) δ 9.64 (2P), 19.79 (1P).

EXAMPLE 3

Preparation of N-(2-pyridylmethyl)-N',N'',N'''-tris(methylenephosphonic acid propyl ester)-1,4,7,10-tetraazacyclododecane (PD3PP)

N-(2-pyridylmethyl)-N',N'',N'''-tris(methylenedipropylphosphonate)- 1,4,7,10-tetraazacyclododecane, 0.71 g (0.89 mmol), prepared in Example C, was combined with 3 mL of 0.1M potassium hydroxide and heated at reflux for 18 hr. After cooling to room temperature, the aqueous solution was filtered, and freeze-dried to give a brown residue, which was redissolved into $CH_2Cl_2/C_2H_5OH$ (95:5) and filtered. Following evaporation of solvent and concentration in vacuo, the product was isolated as a brown solid and further characterized by:

$^1H$ NMR ($D_2O$, 353 K) δ 1.24–1.36 (m, 9H), 1.95–2.04 (m, 6H), 3.03–3.29 (m, 22H), 4.10–4.25 (m, 8H), 7.74–7.92 (m, 2H), 8.23– 8.29 (m, 1H), 8.87–8.96 (m, 1H); and $^{13}C$ {$^1H$} NMR ($D_2O$, 353 K) δ 13.15, 27.20, 50.43, 53.89, 54.48, 54.98, 55.42, 64.33, 69.41, 126.38, 128.30, 141.24, 152.46, 161.45; and $^{31}P$ {$^1H$} NMR ($D_2O$, 353K) δ 21.61 (2P), 21.95 (1P).

Complexes: Preparation of metal/ligand complexes for biodistribution studies.

General Procedure

Metal ligand complexes were prepared by various methods. The methods included mixing of the metal and ligand in aqueous solution and adjusting the pH to the desired value. Complexation was done in solutions containing salts and/or buffers as well as water. Sometimes heated solutions were found to give higher complex yields than when the complexation was done at ambient temperatures.

For example, a solution of the ligand is prepared by dissolving the ligand in deionized water (about pH=2). A ligand/metal complex was then prepared by combining the ligand solution with aqueous $SmCl_3.H_2O$ ($3\times10^{-4}M$ in 0.01N HCl) containing tracer $^{153}SmCl_3$. After thorough mixing, the percent metal as a complex was determined by passing a sample of the complex solution through a Sephadex™ column, eluting with 4:1 saline (0.85% NaCl/$NH_4OH$), and collecting 2×3 mL fractions. The amount of radioactivity in the combined elutions was then compared with that left on the resin. Under these conditions, complex was removed with the eluent and non-complexed metal is retained on the resin. By this method complexation was determined to usually be about 95% or greater.

Using the above procedure, the complexes of samarium with

N-(2-pyridylmethyl)-N',N'',N'''-triacetic acid- 1,4,7,10-tetraazacyclododecane (PD3A);

N-(2-pyridylmethyl)-N',N'',N'''-tris(methylenephosphonic acid ethyl ester)-1,4,7,10-tetraazacyclododecane (PD3EP);

N-(2-pyridylmethyl)-N',N'',N'''-tris(methylenephosphonic acid propyl ester)-1,4,7,10-tetraazacyclododecane (PD3PP); and N-(2-pyridylmethyl)-N',N'',N'''-tri(methylenephosphonic acid-1,4,7,10-tetraazacyclododecane (PD3P);

were made. Complexes with gadolinium are made in a similar manner.

The following tables illustrate the kinetic inertness of the Sm complexes derived from PD3A, PD3PP and PD3EP.

| pH | % Complex |
|---|---|
| pH Stability Profile of $^{153}$Sm-PD3A | |
| 1 | 98.30 |
| 2 | 99.38 |
| 4 | 99.62 |
| 7 | 99.86 |
| 9 | 99.86 |
| 11 | 99.80 |
| 14 | 99.96 |
| pH Stability Profile of $^{153}$Sm-PD3PP | |
| 1 | 72.52 |
| 3 | 87.56 |
| 5 | 92.99 |
| 7 | 95.06 |
| 9 | 95.22 |
| 11 | 92.74 |
| 14 | 87.65 |
| pH Stability Profile of $^{153}$Sm-PD3EP | |
| 1 | 78.95 |
| 3 | 93.80 |
| 5 | 93.02 |
| 7 | 93.77 |
| 9 | 95.89 |
| 11 | 95.77 |
| 14 | 94.07 |

BIODISTRIBUTION

General Procedure

Sprague Dawley rats were allowed to acclimate for five days then injected with 100 μL of the complex solution via a tail vein. The rats weighed between 150 and 200 g at the time of injection. After 30 min. the rats were killed by cervical dislocation and dissected. The amount of radioactivity in each tissue was determined by counting in a NaI scintillation counter coupled to a multichannel analyzer. The counts were compared to the counts in 100 μL standards in order to determine the percentage of the dose in each tissue or organ.

The percent dose in blood was estimated assuming blood to be 6.5% of the total body weight. The percent dose in bone was estimated by multiplying the percent dose in the femur by 25. The percent dose in muscle was estimated assuming muscle to be 43% of the total body weight. The number of rats used in the average is n.

In addition to organ biodistribution, chelates of the compounds of Formula (I) were evaluated for efficiency of bone localization since phosphonates are known for their ability to bind to hydroxyapatite. The results of these tests are given below.

EXAMPLE I

When the complex $^{153}$Sm[N-(2-pyridylmethyl)-N',N'', N'''-tris(methylenephosphonic acid ethyl ester)- 1,4,7,10-tetraazacyclododecane] ($^{153}$Sm-PD3EP) was evaluated, the results are given in Table I below. The numbers represent the average of a minimum of 2 rats per data point at 2 hours post injection.

TABLE I

BIODISTRIBUTION OF $^{153}$Sm-PD3EP
% INJECTED DOSE

| ORGAN | AVERAGE |
|---|---|
| Bone | 0.82 |
| Liver | 0.36 |
| Kidney | 1.24 |
| Spleen | 0.01 |
| Muscle | 0.62 |

TABLE I-continued

BIODISTRIBUTION OF $^{153}$Sm-PD3EP
% INJECTED DOSE

| ORGAN | AVERAGE |
|---|---|
| Blood | 0.45 |
| Heart | 0.01 |
| Lung | 0.02 |
| Brain | 0.01 |
| Urine | 97.00 |

EXAMPLE II

When the complex $^{153}$Sm[N-(2-pyridylmethyl)-N',N'', N'''-tris(methylenephosphonic acid propyl ester)- 1,4,7,10-tetraazacyclododecane] ($^{153}$Sm-PD3PP) was evaluated, the results are given in Table II below. The numbers represent the average of a minimum of 3 rats per data point at 2 and 24 hours post injection.

TABLE II

BIODISTRIBUTION OF $^{153}$Sm-PD3PP
% INJECTED DOSE

| ORGAN | AVERAGE 2 hrs | AVERAGE 24 hrs |
|---|---|---|
| Bone | 5.93 | 12.39 |
| Liver | 20.36 | 2.31 |
| Kidney | 0.86 | 0.89 |
| Spleen | 1.19 | 0.22 |
| Muscle | 0.82 | 0.27 |
| Blood | 0.68 | 0.03 |
| Heart | 0.04 | 0.02 |
| Lung | 0.20 | 0.40 |
| Brain | 0.04 | 0.00 |
| Stomach | 1.39 | 0.04 |
| Small intestine | 13.56 | 0.13 |
| Large Intestine | 0.18 | 0.16 |
| Urine | 50.00 | 83.00 |
| Feces | — | 5.33 |

Other embodiments of the invention will be apparent to those skilled in the art from a consideration of this specification or practice of the invention disclosed herein. It is intended that the specification and examples be considered as exemplary only, with the true scope and spirit of the invention being indicated by the following claims.

What is claimed is:

1. 2-Pyridylmethylenepolyazamacrocyclic compounds of the formula

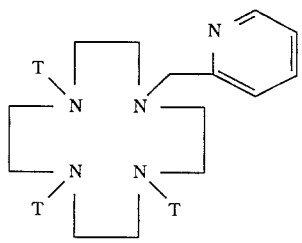
(I)

wherein:

T is independently —CH$_2$—COOH,

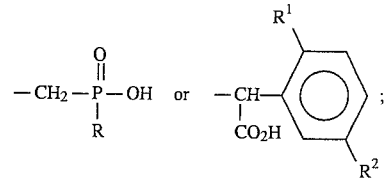

where:

R is OH, C$_1$-C$_5$ alkyl or —O—(C$_1$-C$_5$ alkyl);
R$^1$ is OH or OCH$_3$;
R$^2$ is NO$_2$, NH$_2$, isothiocyanato, semicarbazido, thiosemicarbazido, maleimido, bromoacetamido or carboxyl;
with the proviso that only one T moiety can be

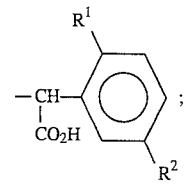

where R$^1$ and R$^2$ are defined as before; and
with the proviso that at least one T moiety is —CH$_2$—P(O)ROH where R is —O—(C$_1$-C$_5$ alkyl); or pharmaceutically-acceptable salts thereof.

2. A compound of claim 1 wherein from one to three T equal —CH$_2$—P(O)ROH, where R is —O—(C$_1$-C$_5$ alkyl), or pharmaceutically-acceptable salts thereof.

3. A compound of claim 2 wherein R is ethoxy, or pharmaceutically-acceptable salts thereof, and is named as N-(2-pyridylmethyl)-N',N'',N'''-tris(methylenephosphonic acid ethyl ester)-1,4,7,10-tetraazacyclododecane.

4. A compound of claim 2 wherein R is propoxy, or pharmaceutically-acceptable salts thereof, and is named as N-(2-pyridylmethyl)-N',N'',N'''-tris(methylenephosphonic acid propyl ester)-1,4,7,10-tetraazacyclododecane.

5. A compound of claim 1 where one T is

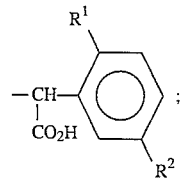

where R$^1$ and R$^2$ are defined as in claim 1; and the other T terms are defined as in claim 1.

6. A complex which comprises a polyazamacrocyclic compound of the formula

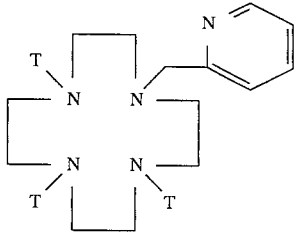
(I)

wherein:

T is independently —CH$_2$—COOH,

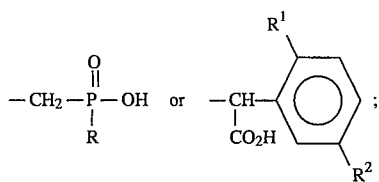

where:

R is OH, C$_1$–C$_5$ alkyl or —O—(C$_1$–C$_5$ alkyl);

R$^1$ is OH or OCH$_3$;

R$^2$ is NO$_2$, NH$_2$, isothiocyanato, semicarbazido, thiosemicarbazido, maleimido, bromoacetamido or carboxyl;

with the proviso that only one T moiety can be

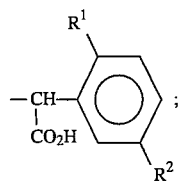

where R$^1$ and R$^2$ are defined as before; and with the proviso that at least one T moiety is —CH$_2$—P(O)ROH where R is —O—(C$_1$–C$_5$ alkyl); or pharmaceutically-acceptable salts thereof;

complexed with a metal ion selected from Gd$^{+3}$, Mn$^{+2}$ or Fe$^{+3}$.

7. A complex of claim 6 wherein the metal is Gd$^{+3}$.

8. A complex of claim 6 wherein from one to three T equal —CH$_2$—P(O)ROH, where R is —O—(C$_1$–C$_5$ alkyl), and the metal is Gd$^{+3}$.

9. A pharmaceutical formulation comprising a complex of claim 6 with a pharmaceutically-acceptable carrier.

10. A method for diagnosis using magnetic resonance imaging of a disease state associated with calcific, brainy heart or liver tissue, or variations in blood pool or general perfusion in an animal which comprises administering to said animal an effective amount of the formulation of claim 9.

11. A method of claim 10 wherein the formulation comprises a complex as defined in claim 8.

12. A method of claim 11 wherein the complex comprises a compound N-(2-pyridylmethyl)-N',N",N'''-tris(methylenephosphonic acid ethyl ester)-1,4,7,10-tetraazacyclododecane.

13. A method of claim 11 wherein the complex comprises a compound N-(2-pyridylmethyl)-N',N",N'''-tris(methylenephosphonic acid propyl ester)-1,4,7,10-tetraazacyclododecane.

* * * * *